United States Patent
Evans et al.

(10) Patent No.: US 6,454,793 B1
(45) Date of Patent: Sep. 24, 2002

(54) METHOD AND APPARATUS FOR ESTABLISHING AND MAINTAINING THERAPEUTIC HYPOTHERMIA

(75) Inventors: Scott M. Evans, Santa Ana, CA (US); William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 27 days.

(21) Appl. No.: 09/703,791

(22) Filed: Nov. 2, 2000

Related U.S. Application Data

(63) Continuation of application No. 09/266,452, filed on Mar. 11, 1999.

(51) Int. Cl.[7] .................................................. A61F 7/00
(52) U.S. Cl. ...................... 607/105; 607/106; 607/113; 128/898
(58) Field of Search .................... 607/96, 104, 105, 607/106, 113; 606/20–26; 128/898

(56) References Cited

U.S. PATENT DOCUMENTS

| | | | |
|---|---|---|---|
| 4,747,826 A | 5/1988 | Sassano | |
| 4,850,958 A | 7/1989 | Berry et al. | |
| 4,860,744 A | * 8/1989 | Johnson et al. | ............... 606/21 |
| 4,919,134 A | 4/1990 | Streeter | |
| 5,122,113 A | 6/1992 | Hattler | |
| 5,149,321 A | 9/1992 | Klatz et al. | |
| 5,207,640 A | 5/1993 | Hattler | |
| 5,230,862 A | 7/1993 | Berry et al. | |
| 5,234,405 A | 8/1993 | Klatz et al. | |
| 5,271,743 A | 12/1993 | Hattler | |
| 5,308,320 A | * 5/1994 | Safar et al. | ................. 604/113 |
| 5,395,314 A | 3/1995 | Klatz et al. | |
| 5,501,663 A | 3/1996 | Hattler et al. | |
| 5,514,094 A | 5/1996 | Anello et al. | |
| 5,549,559 A | 8/1996 | Eshel | |
| 5,695,457 A | 12/1997 | St. Goar et al. | |
| 5,800,375 A | 9/1998 | Sweezer et al. | |
| 5,837,003 A | * 11/1998 | Ginsburg | ..................... 606/27 |
| 5,871,526 A | 2/1999 | Gibbs et al. | |
| 5,906,588 A | 5/1999 | Safar et al. | |
| 6,190,356 B1 | 2/2001 | Bersin | |
| 6,231,594 B1 | 5/2001 | Dae | |

FOREIGN PATENT DOCUMENTS

EP   0 853 951 A2   7/1998

OTHER PUBLICATIONS

U.S. patent application Ser. No. 09/266,452, Evans et al., pending.
U.S. patent application Ser. No. 09/477,490, Laserohn et al., pending.
U.S. patent application Ser. No. 09/498,499, Worthen, pending.

* cited by examiner

*Primary Examiner*—Rosiland S. Kearney
(74) *Attorney, Agent, or Firm*—Arlyn Alonzo; John Rogitz

(57) ABSTRACT

A kit for establishing and maintaining hypothermia in a patient for neurotherapeutic purposes includes a high cooling capacity catheter that is advanced into the patient's central venous system to quickly cool the patient to, e.g., 32° C. or so. Once hypothermia has been established, the high capacity catheter is removed and replaced with a lower cooling capacity catheter which maintains a desired reduced temperature. The lower capacity catheter advantageously can be configured as a central venous catheter for permitting the catheter to be used for multiple functions. Alternatively, the high cooling capacity catheter can be used to attenuate a fever and lower the patient's body temperature to normal, with the lower capacity catheter being used to maintain normal body temperature.

5 Claims, 1 Drawing Sheet

METHOD AND APPARATUS FOR ESTABLISHING AND MAINTAINING THERAPEUTIC HYPOTHERMIA
EVANS et al. Serial No.: 09/703,791

METHOD AND APPARATUS FOR ESTABLISHING AND MAINTAINING THERAPEUTIC HYPOTHERMIA

This application is a continuation, of application Ser. No. 09/266,452, filed Mar. 11, 1999.

FIELD OF THE INVENTION

The present invention relates generally to methods and apparatus for cooling patients for therapeutic purposes, and more particularly to systems for treating brain trauma and brain ischemia by inducing hypothermia in a patient.

BACKGROUND

It has been discovered that the medical outcome for a patient suffering from severe brain trauma or from ischemia caused by stroke or heart attack is degraded if the patient's body temperature rises above normal (38° C.). It is further believed that the medical outcome for many such patients might be significantly improved if the patients were to be cooled relatively quickly to around 32° C. for a short period, e.g., 24–72 hours.

The affected organ, in any case, is the brain. Accordingly, systems and methods have been disclosed that propose cooling blood flowing to the brain through the carotid artery. An example of such systems and methods is disclosed in co-pending U.S. patent application Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent application Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system. Moreover, since many patients already are intubated with central venous catheters for other clinically approved purposes anyway, providing a central venous catheter that can also cool the blood requires no additional surgical procedures for those patients. A cooling central venous catheter is disclosed in the present assignee's co-pending U.S. patent application Ser. No. 09/253,109 filed Feb. 19, 1999 and incorporated herein by reference.

The present invention recognizes that a patient requiring hypothermia preferably be cooled down rapidly, at a rate of two degrees or more an hour. Thus, catheters with high cooling capacities, such as the catheter that is the subject of the second of the above-referenced applications, are desirable. As- recognized herein, however, it is not necessary to maintain a high capacity catheter in a patient once the patient has been cooled, provided a catheter with lower cooling capacity is used to maintain temperature at the desired level. The present invention understands that such a lower cooling capacity catheter, which can be configured as, e.g., a central venous catheter to facilitate uses other than just cooling, can be advantageously used to replace the higher capacity catheter to maintain temperature.

SUMMARY OF THE INVENTION

A kit for lowering and maintaining a feverish patient's temperature to normal body temperature or below includes a first catheter that has at least one fluid circulation passageway connectable to a source of coolant. In accordance with the present invention, the first catheter is configured for placement in a patient's circulatory system, and the first catheter is characterized by a first cooling capacity. Also, a second catheter has at least one fluid circulation passageway connectable to a source of coolant. As set forth below, the second catheter is configured for placement in a patient's circulatory system, with the second catheter having a second cooling capacity that is less than the first cooling capacity.

In a preferred embodiment, the kit can include the source of coolant. Preferably, the source of coolant includes at least one thermal electric cooler (TEC) for heating or cooling coolant such that coolant is returned to the catheter to heat or cool the catheter.

In a particularly preferred embodiment, the first catheter includes a heat exchange region that in turn includes at least one hollow fiber. Moreover, the second catheter is configured as a central venous catheter, and it includes a heat exchange region that includes at least one balloon.

In another aspect, a method for establishing and maintaining normal body temperature or hypothermia in a patient includes establishing the desired temperature in the patient using a high cooling capacity catheter placed in the venous system of the patient. The desired temperature is then maintained in the patient using a central venous catheter having a heat exchange region.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
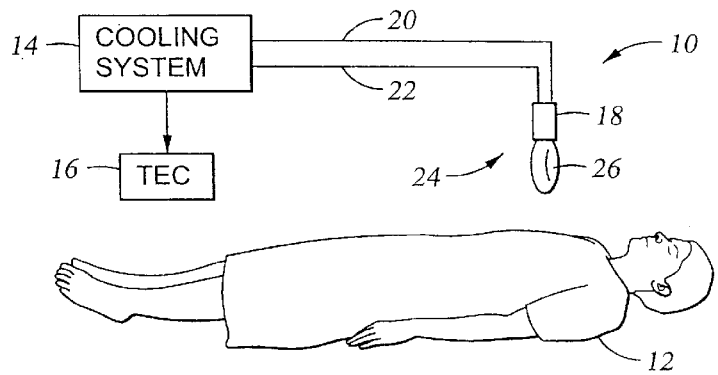
FIG. 1 is a schematic view of the cooling system using the high cooling capacity catheter.
Figure 2:
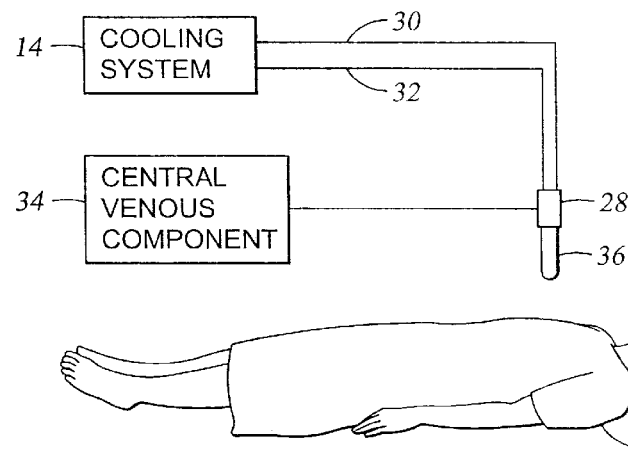
FIG. 2 is a schematic view of the cooling system using the low cooling capacity central venous catheter.

Referring initially to FIG. 1, a therapeutic system, generally designated 10, is shown for establishing and maintaining hypothermia in a patient 12, or for attenuating a fever spike in a patient and then maintaining normal body temperature in the patient. As shown, the system 10 includes a cooling system 14 that can be a water-bath system such as the system disclosed in the present assignee's co-pending U.S. patent application Ser. No. 09/220-,897 filed Dec. 28, 1998 and incorporated herein by reference, or a cooling system including at least one thermal electric cooler (TEC) 16, as disclosed in the present assignee's co-pending U.S. patent application Ser. No. 09/260,950, now U.S. Pat. No. 6,019,783 filed Mar. 1, 1999 and incorporated herein by reference. In any case, the cooling system 14 can be considered a source of coolant, preferably sterile saline, for the catheters of the present invention.

As set forth in these applications, the cooling system 14 can include a heat exchanger, a pump, and, if desired, a controller. Preferably, the pump is a peristaltic pump, but other types of positive displacement pumps, such as but not limited to piston pumps and gear pumps, or even centrifugal pumps, can be used. A peristaltic pump is preferred in the present implementation because it can pump coolant without directly contacting the coolant, but instead simply by squeezing a tube through which the coolant flows. In this way, the pump is reusable, and only the present catheters and portions of the system 10 coming in direct contact with the coolant need be made disposable to render an advantageously disposable and sterile coolant delivery system. The controller controls the rate at which coolant is pumped by the pump and, if desired, the rate at which heat is added or subtracted from the coolant. The controller can be implemented by a software-executing processor or by discrete logic circuits or other electronic circuitry device to establish a desired patient temperature by appropriately controlling the pump and/or heat exchanger in response to a temperature signal derived from a sensor in the patient 12.

As shown in FIG. 1, a high cooling capacity catheter 18 can communicate with the cooling system 14 via coolant supply and return lines 20, 22. The coolant lines 20, 22 can be IV lines or tubes or other suitable fluid conduits, such as metal (steel) tubes. When the coolant lines 20, 22 are plastic tubes, they can be connected to the catheter 18 and the cooling system 14 by suitable connecting structure, such as Luer fittings, interference fits, solvent bonding, heat staking, ultrasonic welding, and the like.

The high cooling capacity catheter 18 includes a heat exchange region 24 that in turn includes one or more hollow fibers 26, as disclosed in the above-referenced U.S. patent application Ser. No. 09/133,813. As set forth in the '813 application, coolant is circulated in a closed fluid communication loop between the hollow fibers 26 and cooling system 14 to remove heat from the patient 12. By "high cooling capacity" is meant the ability to cool down a 150 pound mammal from normal body temperature to about 6° C. below normal body temperature at a rate of at least one and one-half degrees per hour (1.5° C./hr.). As set forth in greater deta below, the high capacity catheter 18 is advanced (preferably through an introducer sheath) into the patient 12 to establish hypothermia in the patient 12, or to attenuate a fever back to normal body temperature. Preferably, the catheter 18 is advanced into the central venous system, and more preferably into the vena cava, either through the saphenous vein or jugular vein or femoral vein.

Once hypothermia or non-elevated temperature has been established, the high capacity catheter 18 can be removed from the patient, and temperature maintained at a desired normal or hypothermic level by using a lower (relative to the capacity of the high capacity catheter 18) cooling capacity catheter 28. In the preferred embodiment, the lower capacity catheter 28 is configured for use as a central venous catheter, and can be embodied by the catheter disclosed in the above-referenced patent application Ser. No. 09/253,109, filed Feb. 19, 1999. Accordingly, the lower capacity catheter 28 can communicate with the cooling system 14 via coolant supply and return lines 30, 32. Also, the lower capacity catheter 28 can communicate with one or more central venous components 34, such as IV infusion devices, drug delivery syringes, blood withdrawal devices, and so on as are commonly used in connection with central venous catheters for undertaking respective central venous catheter functions.

As disclosed in the referenced application Ser. No. 09/253,109 filed Feb. 19, 1999, the lower capacity catheter 28 includes a heat exchange region. In the preferred embodiment, the heat exchange region is established by one or more balloons 36, although it could be established by hollow fibers in the manner of the catheter 18, but on a smaller scale. The catheter 28 can be advanced into the superior vena cava through the jugular vein or subclavian vein to cool the patient 12 by means of coolant circulating in a closed loop between the cooling system 14 and the balloon 36. As mentioned above, the lower capacity catheter 28 can also be used to undertake conventional central venous catheter functions.

Figure 3:
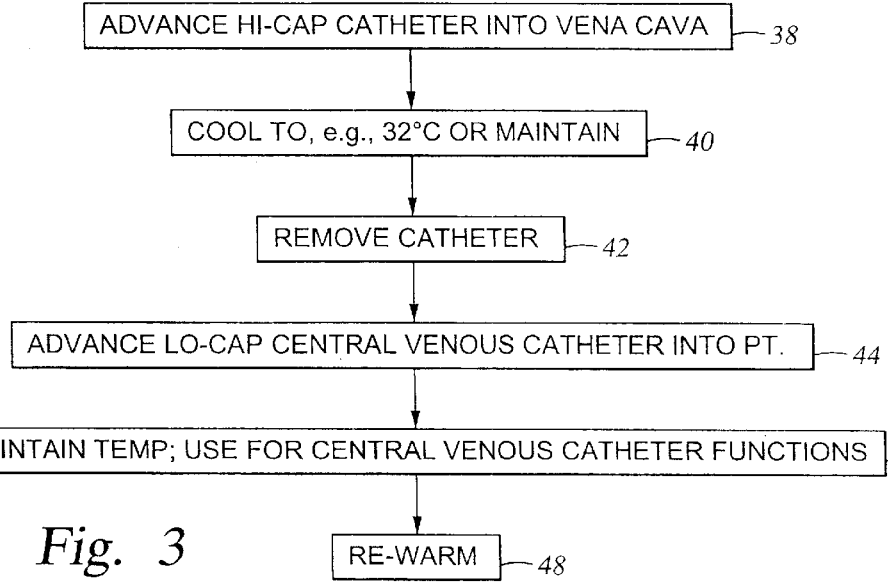
FIG. 3 is a flow chart of the present invention for establishing and maintaining hypothermia in a patient.

The process of the present invention can be appreciated in reference to FIG. 3. Commencing at block 38, the high capacity catheter 18 is advanced into the vena cava of the patient 12. The patient 12 is relatively quickly and precisely cooled to, e.g., 32° C.–34° C. using the high capacity catheter 18 at block 40 when hypothermia is indicated as a treatment. Or, when it is desired merely to attenuate a fever spike, the patient can be relatively quickly and precisely cooled to 38° C. In any event, to effect a "soft landing" to the desired temperature, as the body temperature approaches the desired level warm coolant can be circulated through the catheter 18 in lieu of cold coolant.

Once the desired body temperature has been established, the high capacity catheter 18 is removed at block 42, and the lower capacity catheter 28 advanced into the vena cava at block 44, it being understood that the step at block 42 can be omitted if desired and both catheters 18, 28 be present simultaneously in the patient. Moving to block 46, the desired patient temperature is maintained using the lower capacity catheter 28.

Also, when the catheter 28 is configured as a central venous catheter, it can be used to undertake the central venous catheters mentioned above. At block 48, when hypothermia has been induced and treatment is completed, the patient is rewarmed to normal body temperature by circulating warm coolant through the catheter 28.

While the particular Method and Apparatus for patient Temperature control as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. A method for establishing and maintaining a desired temperature in a patient, comprising the acts of:
   lowering the patient's temperature using a first catheter placed in the venous system of the patient; and
   maintaining the temperature at a desired level using a central venous catheter having a heat exchange region, the central venous catheter being different from the first catheter.

2. The method of claim 1, wherein the high cooling capacity catheter includes at least one hollow fiber.

3. The method of claim 1, wherein the heat exchange region of the central venous catheter includes at least one balloon.

4. The method of claim 1, comprising the act of removing the high capacity catheter from the patient prior to the maintaining act.

5. The method of claim 1, comprising the act of undertaking one or more central venous line functions using the central venous catheter during the maintaining act.

* * * * *